United States Patent [19]

Stein et al.

[11] Patent Number: 5,070,519
[45] Date of Patent: Dec. 3, 1991

[54] SELECTIVE EQUALIZATION RADIOGRAPHY

[75] Inventors: Jay A. Stein, Framingham, Mass.; Donald B. Plewes, Port Credit, Canada; Russell J. Gershman, Middleborough, Mass.; James G. Liebau, Boston, Mass.; John N. Williams, Concord, Mass.

[73] Assignee: Hologic, Inc., Waltham, Mass.

[21] Appl. No.: 592,841

[22] Filed: Oct. 4, 1990

[51] Int. Cl.⁵ .............................................. G21K 5/10
[52] U.S. Cl. ..................................... 378/146; 378/99; 378/108; 378/145; 358/111
[58] Field of Search ............... 378/145, 146, 156, 155, 378/99, 151, 108; 358/111

[56] References Cited

U.S. PATENT DOCUMENTS

| | | | |
|---|---|---|---|
| 4,032,787 | 6/1977 | Albert | 378/99 |
| 4,247,780 | 1/1981 | Webber et al. | 378/99 |
| 4,831,260 | 5/1989 | Dibianca | 378/108 |
| 4,868,857 | 9/1989 | Dobbins, III | 378/99 |
| 4,947,416 | 8/1990 | McFaul et al. | 378/146 |
| 4,953,189 | 8/1990 | Wang | 378/108 |
| 4,953,192 | 8/1990 | Plewes | 378/146 |
| 4,972,458 | 11/1990 | Plewes | 378/146 |

OTHER PUBLICATIONS

Plewes, D. B., Computer Assisted Exposure in Scanned Film Radiography, Proceedings International Workshop on Physics and Engineering in Medical Imaging, Mar. 1982, pp. 79–86.

Primary Examiner—Edward P. Westin
Assistant Examiner—Kim-Kwok Chu
Attorney, Agent, or Firm—Cooper & Dunham

[57] ABSTRACT

An equalization radiography system automatically identifies the lung field in a pre-scan and then carries out an imaging scan in which it equalizes the X-ray exposure but only outside the lung field.

20 Claims, 8 Drawing Sheets

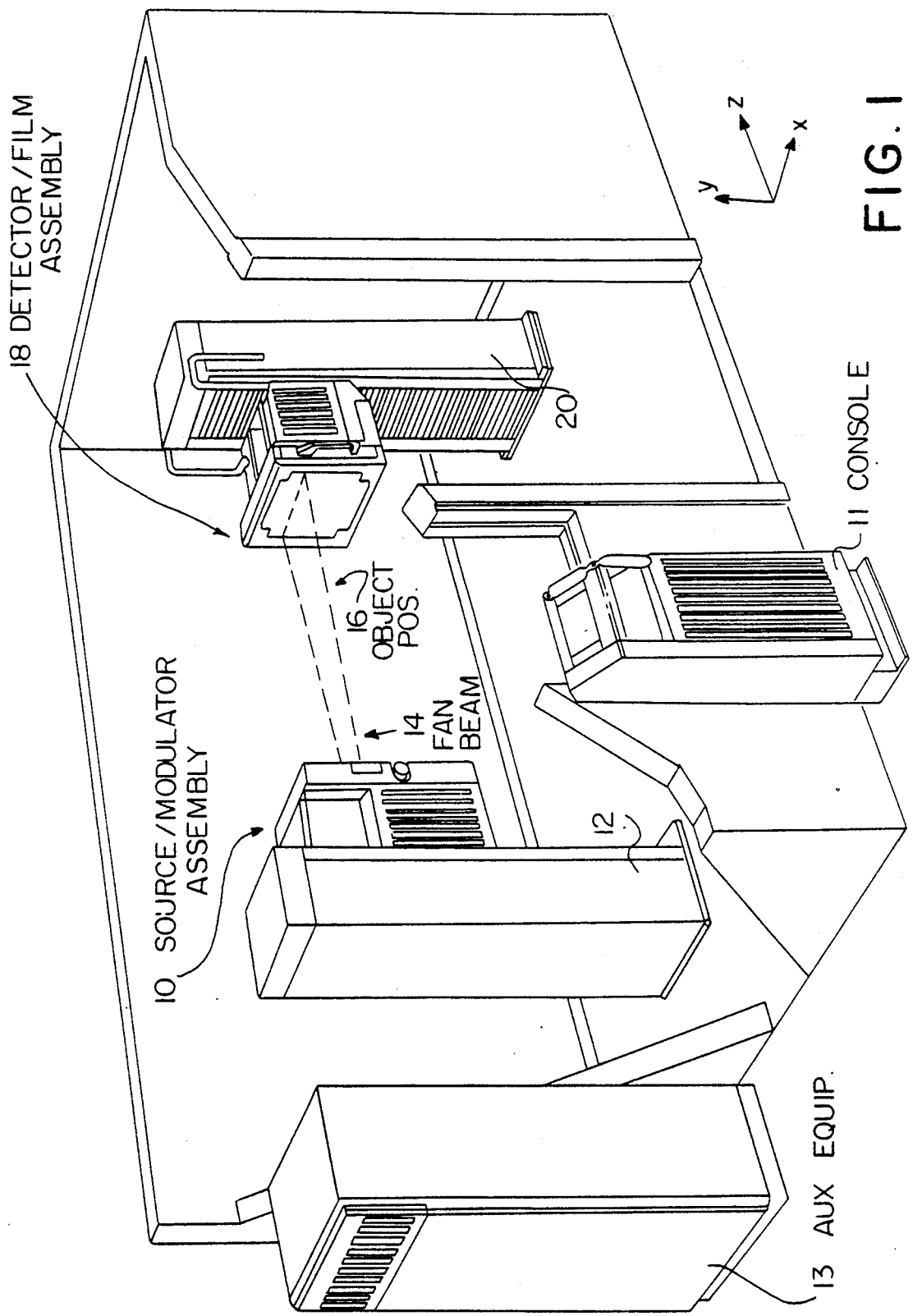

SELECTIVE EQUALIZATION RADIOGRAPHY

FIELD AND BACKGROUND OF THE INVENTION

The invention relates to radiography and particularly to equalized radiography which improves diagnostic capabilities by locally varying the radiation incident on the object to expose denser parts to more radiation and thereby to image all parts well despite limitations in the dynamic range and other characteristics of the imaging medium. More specifically, the invention pertains to selective equalization radiography which improves image quality by equalizing different fields of the image differently. A special case is exposing the lung field uniformly while equalizing other fields.

In conventional radiography, image quality and diagnostic value can be compromised when the object x-ray transmission variations exceed the limits of the imaging medium. For example, a good x-ray image of the lung field typically leaves the mediastinum and retrocardiac areas underexposed; if those areas are exposed well, then the lung field is overexposed. Equalization radiography can overcome such problems and can improve image quality and diagnostic value by varying the local x-ray exposure to compensate for local variations in the object's x-ray transmission. Such radiography is discussed in the commonly assigned Wang European Patent Application No. 86308224.4 and Aitkenhead and Gershman U.S. patent application Ser. No. 07/525,498 filed on May 18, 1990, as well as in Plewes U.S. Pat. No. 4,773,087 and U.S. patent application Ser. No. 07/242,644 filed Sept. 13, 1988. See, also, U.S. Pat. Nos. 4,675,893, 4,715,056, 4,677,652, and 4,741,012. All of the documents cited in this paragraph are hereby incorporated by reference in this specification. Further background material concerning the subject can be found in the documents made of record in the patents and applications cited in this paragraph.

In an exemplary equalization system, an x-ray fan shaped beam scans the patient and a modulator locally controls the x-rays before they reach the patient in order to modulate the radiation differently as between different sectors of the fan shaped and as between different stages of the scanning movement. The degree and kind of local modulation are under the control of a feedback circuit which locally measures the x-rays in the fan shaped exiting the object. The goal of this local, time varying modulation is to equalize the image by reducing the difference in exposure as between different areas at the image plane. The modulator can use a row of modulator elements which are individually and selectively movable into the x-ray beam to vary it locally such as by varying the local attenuation, the local beam cross-section, and/or the local exposure time of the x-rays impinging on the object.

An earlier proposal is discussed in Plewes, D. B., Computer Assisted Exposure In Scanned Film Radiography, Proceedings International Workshop On Physics and Engineering In Medical Imaging, March, 1982, pages 79–86. This proposal states at page 82, in connection with FIGS. 5 and 8, that while equalization may be helpful for nodule detection it may be detrimental for looking at diseases manifested by diffuse opacifications and for such a case the system feedback could be adjusted to maintain low spatial frequency over the lung field alone. The proposal shows in FIG. 5 a relationship setting forth a "conventional image" for the lung field and shows the result of a related experiment in FIG. 8. Other parts of the citation might be relevant as well.

While equalized radiography can provide significant improvement in image quality and diagnostic value, it can also introduce some image artifacts, as noted for example in Plewes, D. B. and Vogelstein, E., Exposure Artifacts in Raster Scanned Equalization Radiography, Med. Phys. Vol. 11. pp. 158–165 (1984) and in Vlasbloem, et al., RADIOLOGY, Vol. 169, pages 29–34 (October 1988). See, also, Plewes, D. B. et al., Maximizing Film Contrast For Scanning Equalization Radiography, Medical Physics, Vol. 17, No. 3, May/June 1990, pages 357–361, as well as the documents cited therein.

SUMMARY OF THE INVENTION

An object of the invention is to improve equalization radiography. A more specific object is to reduce image artifacts in selected fields such as the lung field. A still more specific object is to improve equalization radiography by identifying and exposing selected fields without equalization or under different equalization.

In an exemplary and non-limiting embodiment of the invention, first a low-intensity beam of penetrating radiation scans the object to identify a selected field (e.g., the lung field) and to derive other information for a second scan. Then, a higher-intensity beam scans while being modulated in a desired manner outside the selected field. In the selected field, the beam exposes the object substantially uniformly. This equalizes the image where desired but delivers constant exposure where preferred. As an alternative, the selected field can also be equalized, but differently from other fields.

More specifically, in an exemplary embodiment an x-ray source/modulator assembly generates a fan shaped beam which is thin in the vertical direction and wide in the horizontal direction. In a first scan, the beam is set at a constant low intensity and sweeps vertically across the object while a detector/film assembly measures the object-attenuated beam to determine how to set various parameters for a second scan. In the second scan, a higher intensity beam of the same general shape sweeps vertically. However, this time its sectors are selectively and individually modulated to vary locally the exposure delivered to the object in order to equalize the exposure delivered to the image plane everywhere except at a selected field such as the lung field. The same technique can be used in accordance with the invention while scanning similar beams horizontally rather than vertically or in some other orientation.

The terms "object" and "patient" are used interchangeably in this specification because the invention applies to imaging patients by equalizing everywhere else except at a selected field as well as to imaging inanimate objects in a similar manner.

BRIEF DESCRIPTION OF THE DRAWINGS

FIG. 1 is a perspective view of an equalized radiography system using the invention.

DETAILED DESCRIPTION

Figure 1A:
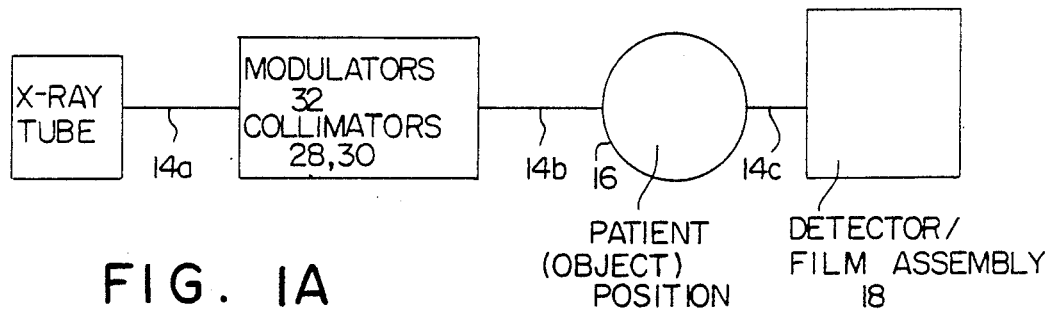
FIG. 1A is a schematic illustration of a part of the system of FIG. 1.
Figure 2:
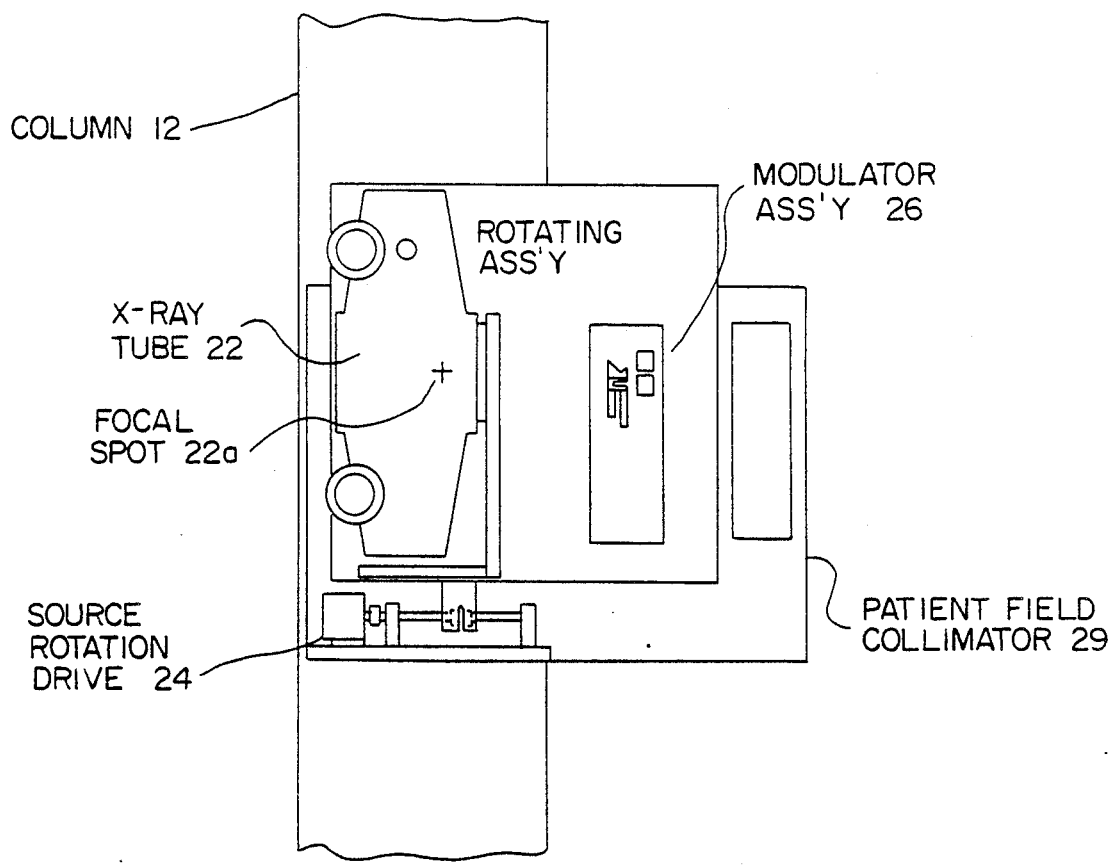
FIG. 2 shows a vertical section of a supporting column and a source/modulator assembly.
Figure 3A:
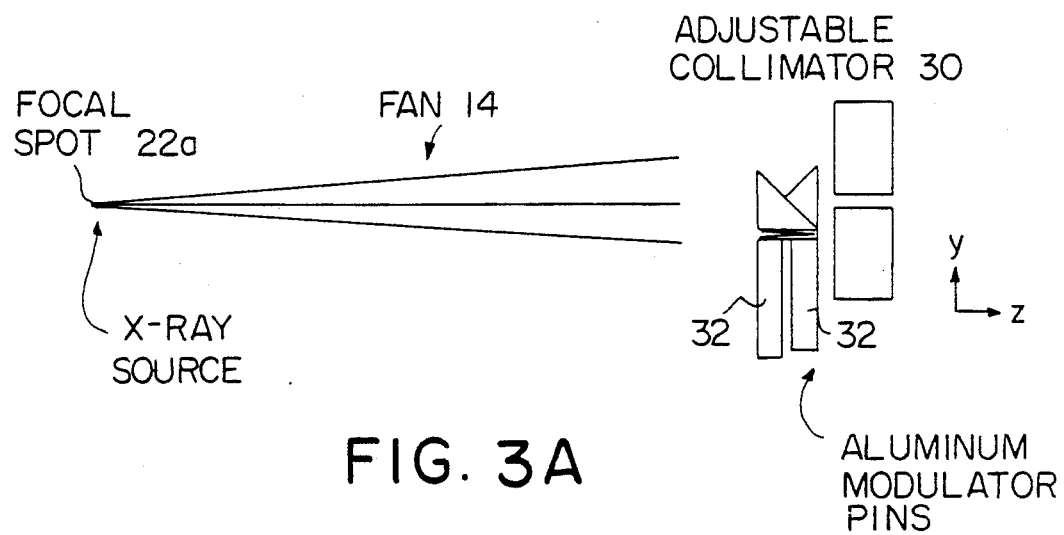
FIG. 3a is a side view and FIG. 3b is a top view of a portion of a modulator assembly, showing modulator pins and a pre-patient collimator.
Figure 3B:
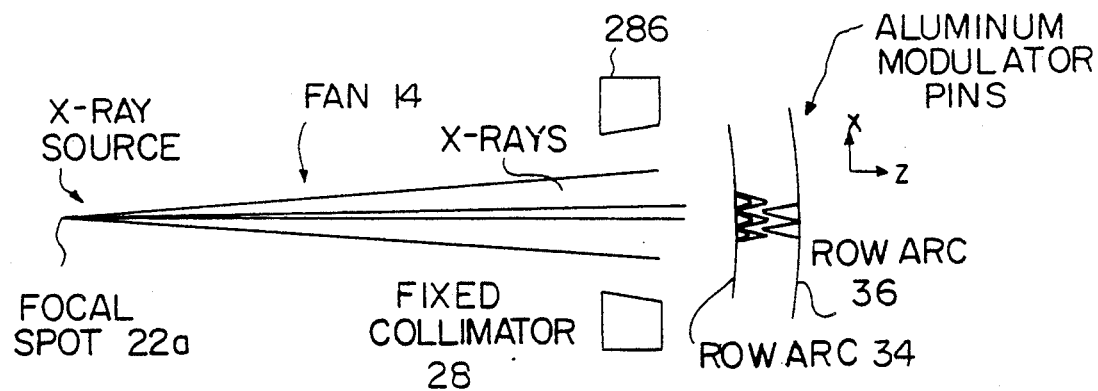
Figure 3C:
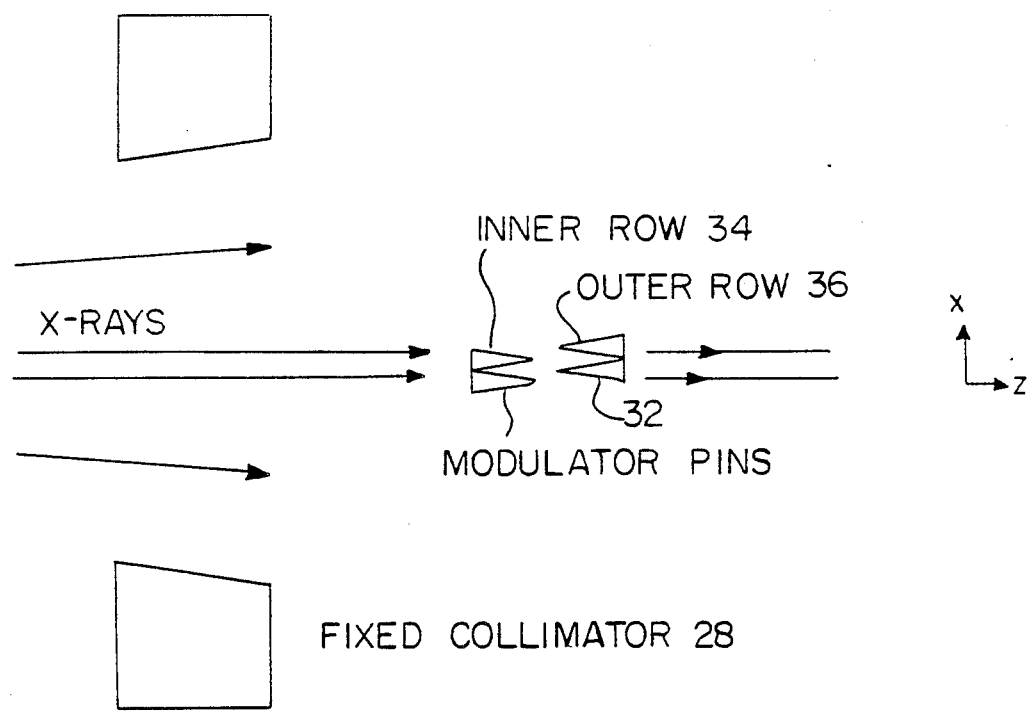
FIG. 3c is a detail of FIG. 3b.
Figure 4:
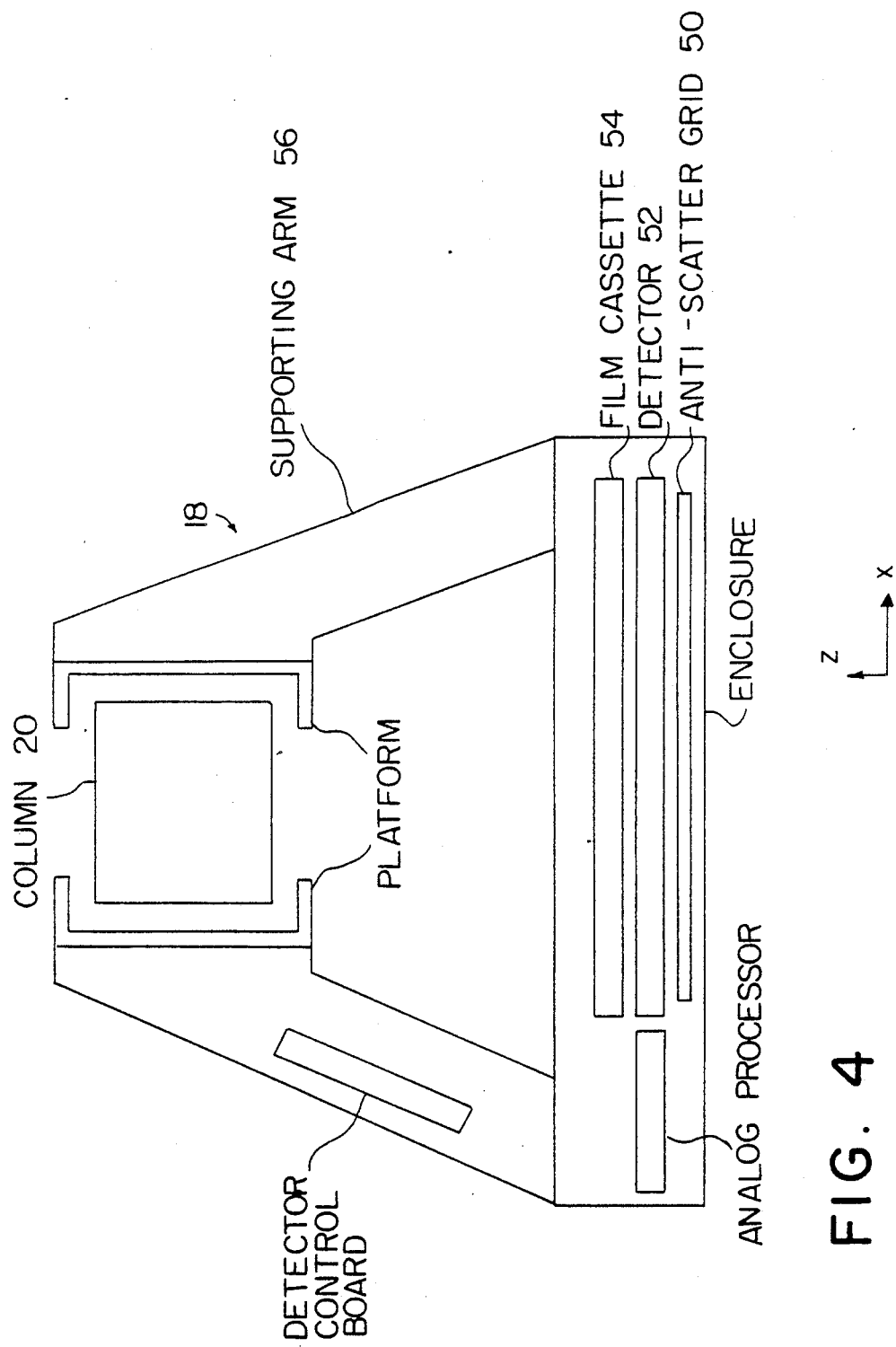
FIG. 4 illustrates a horizontal section of another supporting column and a detector/film assembly.

In a preferred but non-limiting example of the invention, the system is set up for an x-ray exposure by sliding an x-ray source/modulator assembly 10 vertically (in the y-direction) along column 12 to align it with the desired patient field. When energized, assembly 10 generates a fan shaped beam 14 which propagates in the z-direction and is thin in the vertical (y) direction and wide in the horizontal (x) direction and sweeps this beam 14 vertically (either up or down) across an object position 16. Also prior to the x-ray procedure, a detector/film assembly 18 is vertically aligned with source/modulator assembly 10 by sliding it along column 20. As fan shaped beam 14 sweeps vertically across object 16, assembly 18 receives an object-attenuated beam both at a detector 52 and at an x-ray film cassette 54 (FIG. 4). As seen in FIG. 1A, beam 14 can be thought of as being a beam 14a when it emerges from x-ray tube 22, then as a beam 14b after being shaped by collimators 28 and 30 and, if desired, by modulators 32 as well, and as a beam 14c after it is attenuated by an object (if any) at object position 16. In a single-scan mode, detector 52 (FIG. 4) generates a feedback signal to control modulator pins 32 (FIGS. 2 and 3a-3c) which modulate respective sectors of beam 14a in order to reduce the local variation in the exposure which object-attenuated beam 14c delivers at the image plane of film cassette 54. In a dual-scan mode, beam 14a in the first scan is at low intensity and preferably is not modulated, and detector 52 generates a two-dimensional map of the exposure delivered by object-attenuated beam 14c at the detector plane but the x-ray film at cassette 54 does not receive significant exposure. In the second scan, beam 14a is at higher intensity and is locally modulated on the basis of the 2D map derived in the first scan to equalize the exposure which object-attenuated beam 14c delivers at the image plane everywhere except at a selected field. As an alternative, the exposure at the selected field can also be equalized but in a different way from that in the other fields of the image, for example by compressing the exposure range less in the selected field.

As best seen in FIGS. 2 and 3a-3c, source/modulator assembly 10 comprises an x-ray tube 22 rotated in the vertical plane by source rotation drive 24 in order to sweep object 16 with fan shaped 14b, using the focal spot of tube 22 as the center of rotation. Affixed to tube 22 to pivot therewith is a modulator assembly 26. In order to shape the radiation from tube 22 into the desired fan shaped 14b, assembly 26 has a fixed collimator 28 defining the maximum horizontal extent of the fan shaped and a patient field collimator 29 which can be adjusted to define the size of the irradiated, typically rectangular area at the image plane, and further has an adjustable collimator 30 forming a collimator slit that determines the vertical dimension of fan shaped beam 14b. For a given vertical sweep of fan shaped beam 14c across detector/film assembly 18, the setting of patient field collimator 29 typically is fixed so that fan shaped beam 14c at the film plane irradiates only a field of a desired size and shape, e.g., standard x-ray film. The slit aperture of collimator 30 is set depending on factors such as the overall size and expected attenuation properties of the object to deliver the desired overall intensity to the object. For example, the slit aperture can be set to a vertical dimension in the range of 0" to 0.5" at the aperture plane, which corresponds to about 0" to 3.5" at the image plane.

Beam 14c exiting the object impinges on detector/film assembly 18 which, as seen in FIG. 4, comprises the following components arranged in the propagation (z) direction of the x-rays: an anti-scatter grid 50, a detector 52, and a film cassette 54. These elements are mounted on a supporting arm 56 slidably mounted on column 20. Grid 50 can comprise a 12:1 scatter rejection grid for reducing the amount of scattered radiation reaching detector 52. Detector 52 can comprise a flat plate gas ionization detector having an active volume of, e.g., $17 \times 17 \times 0.25"$ filled with an ionizing gas such as Xenon. The electrodes on one side are 70 vertically extending strips 0.23" high and 17" long, separated horizontally by insulating spaces of 0.02". Preferably detector 52 attenuates fan shaped beam 14c as little as possible, e.g., at about 12% attenuation. Film cassette 54 can be a standard $14 \times 17"$ cassette mountable in either orientation.

In order to modulate horizontally spaced sectors of fan shaped beam 14, modulator assembly 26 uses 35 modulator pins 32 which are in generally horizontal inner row 34 and outer row 36 (FIG. 3b) along respective arcs which are centered at the focal spot of tube 22 and are in a plane that includes the focal spot. Pins 32 slide individually and selectively into fan shaped beam 14a in the vertical, y-direction (vertically along the plane of the paper in FIG. 3a and normal to the paper in FIGS. 3b and 3c) such that the pin section in a horizontal plane within fan shaped beam 14a is generally triangular, as illustrated in FIGS. 3b and 3c. This triangular area and the attenuation of a respective beam sector increases as a pin moves further into fan shaped beam 14a.

In the dual-scan mode, where the purpose of the first scan is to derive information for controlling the second scan, beam 14b for the first scan is collimated into a fan shaped beam of the same general shape but preferably is not modulated, and is kept at a low intensity which is sufficient for adequate signal-to-noise ratios at detector 52 but insufficient to cause significant exposure of the film in cassette 54. The desired low intensity can be selected by controlling x-ray tube 22, e.g., by controlling the power supplied to tune 22. It is possible to have some intensity variations in the fan shaped beam during the first scan, so long as they are known or can be measured so that they can be taken into account in deriving the information for controlling the second scan. To derive the information for controlling the second scan, the system uses the signal from detector 52 to generate a two-dimensional map of the transmission of the object at position 16, and from that derives control parameters such as when and how to move each modulator pin 32 during the second scan to achieve the desired selective equalization in which the image is equalized everywhere except at a selected field or is equalized differently at the selected field.

The two-dimensional transmission map from the first scan is determined as follows. Each of the 70 horizontal detector strips "j" of detector 52 outputs signals "$d_{ij}$" during the first scan, where "i" identifies the position of a scan line (i.e., a particular footprint of the wide fan shaped beam 14c on detector 52 over a particular time interval during the first scan) and "j" identifies a particular detector strip of detector 52. If "S" is the x-ray intensity incident on the slit aperture defining beam 14 (and on any modulator pins 32 which are in beam 14), "$m_{ik}$" is the transmission of the k-th modulator pin 32 (a value between 0 and 1), and "$b_{ijk}$" is the amount of signal in the j-th detector strip due to the k-th modulator pin 32 when the pin is fully away from fan shaped beam 14 (a value between 0 and 1), the transmission "$t_{ij}$" of the patient body at object position 16 as measured at the i-th scan line and the j-th detector can be represented as:

$$t_{ij} = d_{ij}/(S)(\Sigma m_{ik}b_{ijk}) \text{ for: } \begin{array}{l} 1 \leq i \leq I \\ 1 \leq k \leq J \end{array} \quad (1)$$

The values of "$d_{ij}$" used in expression 1 are those after the detector strip outputs are processed for gain and offset variations and, if desired, filtered for noise. The gain correction is derived through calibration runs with the modulator pins 32 fully retracted (out of beam 14), and the offset correction is derived by measuring the outputs of the detector strips with x-ray tube 22 off. The values of "$m_{ik}$" are known by keeping track of the position to which the k-th modulator pin is driven for the i-th scan line and from pre-stored information of the value "$m_{ik}$" for each position of each pin 32. The "$b_{ijk}$" values are derived in a calibration run in which the modulator pins 32 are fully retracted out of beam 14 one at a time and beam 14 is scanned and the detector strip outputs "$d_{ij}$" are stored. The system therefore can calculate the 2D map "$t_{ij}$" of the patient's transmission function immediately after the first scan in the dual-scan mode or even in real-time while the first scan is in progress.

Figure 5:
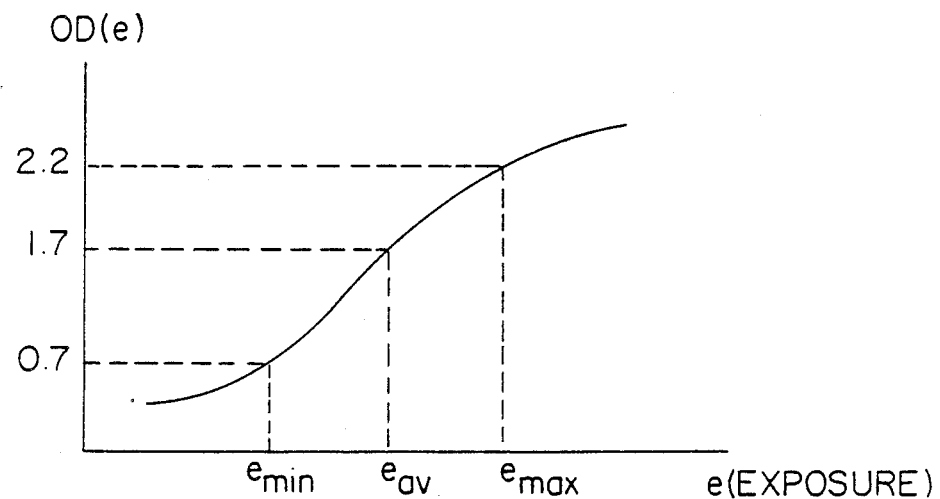
FIGS. 5-9 are graphs useful in explaining an example of the invention.
Figure 6:
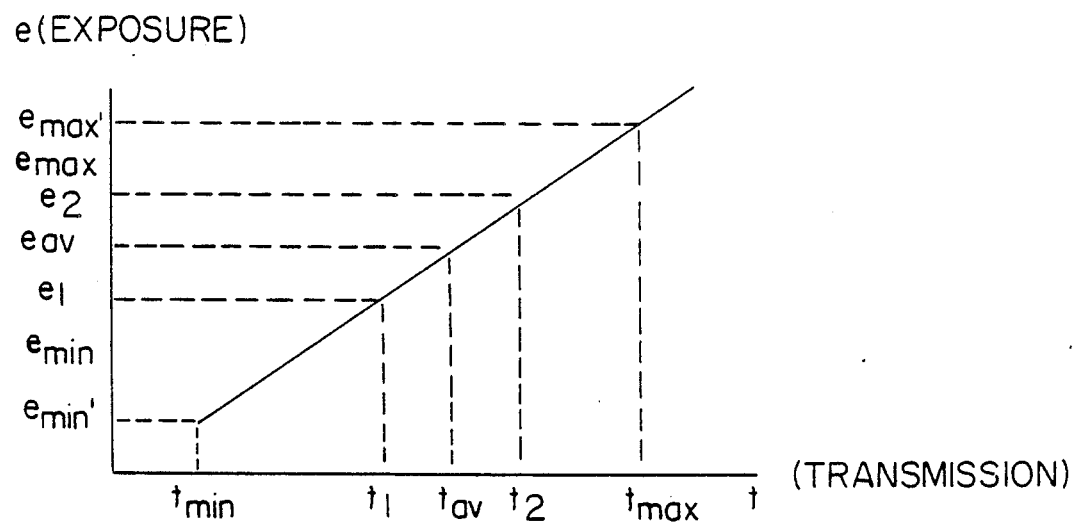
Figure 7:
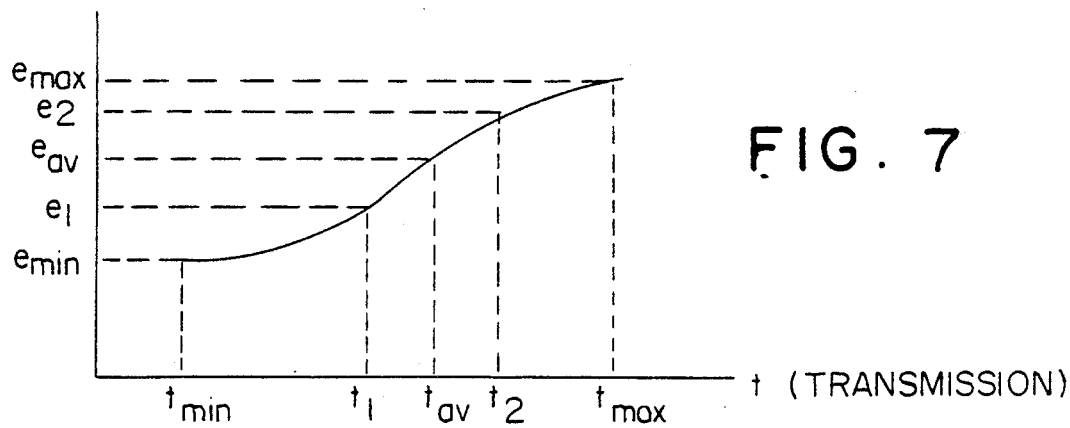

The reason for the 2D map "$t_{ij}$" and the use to which the map is put can be explained by reference to FIGS. 5-9. FIG. 5 illustrates a typical Gamma function of x-ray film, showing the non-linear relationship between exposure level "e" delivered to the x-ray film and optical density "OD(e)" of the x-ray image in a typical film/screen combination. An average level "$e_{av}$" of exposure delivered to the x-ray film produces a desirable optical density OD(e) of, e.g., approximately 1.7 for the lung field. Optical densities OD(e) of 2.2 and 0.7 translate into desired maximum and minimum exposure levels "$e_{max}$" and "$e_{min}$" and can be considered the limits of the exposure delivered to the x-ray film at which images are diagnostically useful. Different film/screen combinations imply different sets of values for the exposure levels $e_{av}$, $e_{max}$ and $e_{min}$ but the same general principles apply. In non-equalized radiography, when the exposure is set correctly for the lung field other areas of the chest would not be imaged in a diagnostically useful way if they are outside the $e_{max}$ and $e_{min}$ limits. The relationship between film/screen exposure and patient body transmission is illustrated in FIG. 6, where if the transmission of the lung field is between $t_1$ and $t_2$ with an average of $t_{av}$, the required corresponding exposures $e_1$ and $e_2$ and $e_{av}$ can all be within the limits of $e_{min}$ and $e_{max}$ of FIG. 5. However, the minimum and maximum of the patient body transmission, $t_{min}$ and $t_{max}$ in this case translate to exposures $e_{min}'$ and $e_{max}'$ delivered to the film, which are outside the limits $e_{min}$ and $e_{max}$ of FIG. 5 and therefore are outside the optical density range OD(e) for diagnostically useful images. By locally varying the exposure delivered to the object to increase it at thick parts of the object to raise $e_{min}'$ and to reduce it at thin parts of the object to lower $e_{max}'$, equalization can in effect compress the range $e_{min}'$ to $e_{max}'$ of the exposure delivered to the film to make it fit within the limits $e_{min}$ and $e_{max}$, as illustrated in FIG. 7.

Figure 8:
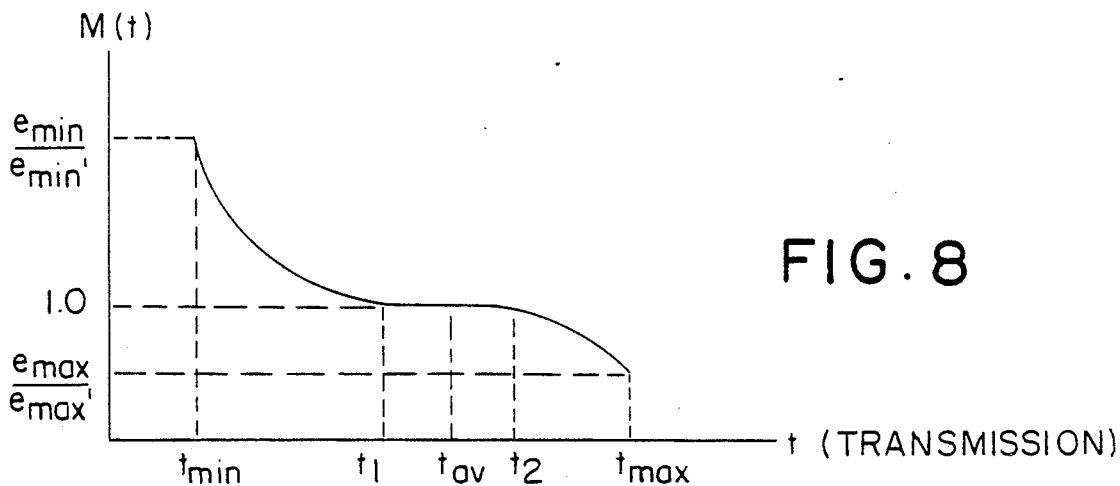

While such equalization could be applied throughout the range of $e_{min}'$ to $e_{max}'$, as in the prior art, the invention takes a different approach in an effort to provide further improvement: it equalizes some but not all areas of the image. As an alternative, it equalizes different fields of the image differently. As seen in FIG. 8, an equalization function in accordance with an example of the invention shows no equalization in the patient transmission range from $t_1$ and $t_2$ which corresponds to the lung field. FIG. 8 shows equalization only outside the lung field. According to FIG. 8, the exposures delivered to the patient and to the film/screen exposure are forced up in the range between $t_{min}$ and $t_1$ and down in the range between $t_2$ and $t_{max}$. The equalization function M(t) of FIG. 8 can be normalized to that illustrated in FIG. 9 to make it corresponds more directly to modulation positions of modulator pins 32.

Figure 9:
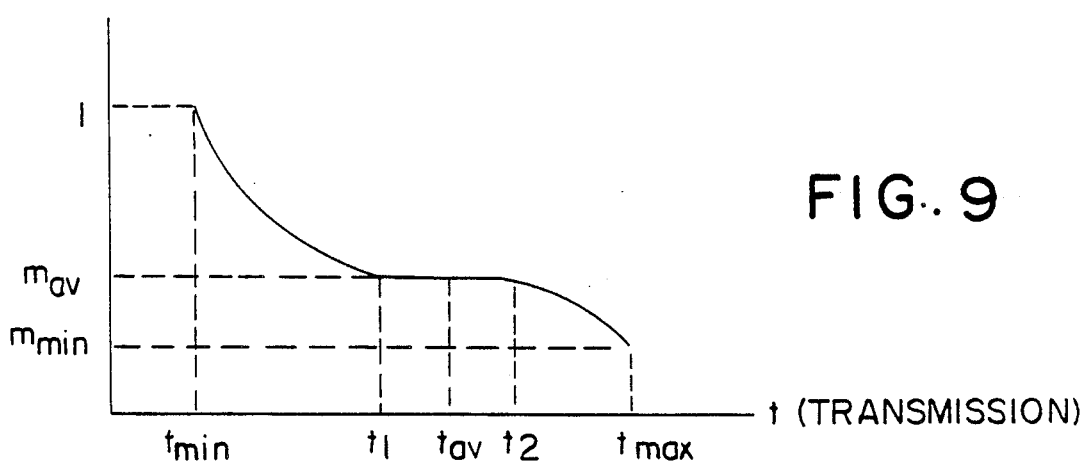

The points $t_{min}$, $t_1$, $t_{av}$, $t_2$ and $t_{max}$ shown in FIG. 9 are all derived from the 2D map $t_{ij}$ discussed above. Known types of smoothing and boundary identification are used to define a coarse mapping of the patient including the lung areas and the mediastinum. From the transmission values $t_{ij}$ in the so-identified lung areas, the upper and lower transmission limits $t_1$ and $t_2$ are identified by a known type of a search process and the average value $t_{av}$ is calculated from the so-identified limits $t_1$ and $t_2$. The largest value of transmission in the so-identified mediastinum is $t_{max}$. To find $t_{min}$, a histogram of the values $t_{ij}$ is constructed which shows a clear demarkation between air and soft tissue and therefore a suitable $t_{min}$.

For the second scan, the system selects an exposure level "S" which is the exposure level at modulator assembly 16 as determined by factors such as the anode current of x-ray tube 22, the fan shaped beam collimation and the exposure time. For the minimum patient body transmission $t_{min}$, "S" is defined by the ratio ($e_{min}/t_{min}$) when all of modulator pins 32 are fully retracted. "S" is calibrated by relying on the relationship e=S when modulator pins 32 are fully retracted (i.e., when m=1). "S" is a term in the approximation e=M(t)*t=S*m(t)*t, where "e" is the exposure at the image plane, "S" is the entrance exposure at modulator assembly 16, "m(t)" is the transmission of a modulator pin (where M(t) ranges from $m_{min}$ and 1, and $m_{min}$ is the smallest transmission value attainable by modulator assembly 16), "t" is the patient's body transmission, and "*" denotes multiplication. When derived in accordance with said approximation, "S" represents the maximum exposure level at modulator assembly 16 which is required to create an equalized exposure $e_{min}$ at the film point imaging the part of the body having the minimum transmission $t_{min}$, for example the densest part of the mediastinum.

In accordance with the example of the invention discussed here, the exposure should be substantially constant over the lung field; hence, the equalization should have a constant value "$m_{av}$" for patient body transmission values corresponding to the lung field. The desired average exposure at the lung field is "$e_{av}$" which corresponds to the desired optical density OD($e_{av}$) of 1.7 for the exemplary screen/film combination discussed here. The modulator transmission "$m_{av}$" required to reduce the exposure S leaving modulator assembly 16 to the level "$e_{av}$" is $m_{av}=e_{av}/(t_{av}*S)$. If "$m_{av}$" is greater than the minimum transmission possible with the modulator, "$m_{min}$", then the modulator has sufficient dynamic range to satisfactorily equalize the patient's attenuation, including actually reducing exposure in areas where the film would be more exposed than at the lung field. For the typical case, the dynamic range of 5:1 (which pins 32 have) is expected to be more than enough to equalize the patient transmission field. If "$m_{av}$" is less than "$m_{min}$", then the modulator does not have enough dynamic range for full equalization. In that case, the factor "S" is determined by a different relationship, namely, $S=e_{av}/(t_{av}*m_{min})$. This relationship forces the exposure level at the lung field to be at the desired level when the modulator is at the minimum transmission $m_{min}$, thus using all of the available dynamic range to equalize the mediastinum.

The modulation function m(t) for the second scan in a preferred embodiment of the invention is defined by the following expression, which corresponds to the curve illustrated in FIG. 9:

$$m(t) = (a/t) + b \qquad (2)$$

where $$a = (1 - m_1)t_1 t_{min}/(t_1 - t_{min});$$
$$b = (m_a t_1 - t_{min})/(t_1 - t_{min})$$
$$\text{for } t_{min} \leq t \leq t_1$$
$$a = (m_a - m_{min})t_2 t_{max}/(t_{max} - t_2);$$
$$b = (m_{min} t_{max} - m_a t_2)/(t_{max} - t_2)$$
$$\text{for } t_{min} \leq t \leq t_1$$

The shape of the modulation function can be modified in specified regions by adding a gain parameter "q" such that $m(t)=(a/t^q+b)$. This modulation function m(t) is specified for each modulator pin 32 for each scan line (where the term scan line denotes the position of fan shaped beam 14c over a short interval of time during the second scan). The system keeps track of which transmission values are associated with which modulator pin 32 because the incidence of the beam sectors defined by the respective modulator pins are specified by the mapping "$b_{ijk}$" discussed earlier. This information has been previously processed by function fitting to find the actual position of the peak of each sector of beam 14c at detector 52 as a function of scan line "i", and this may be represented as an array "p" of elements "$p_{ik}$" which contains the beam sector positions at the detector plane as a function of the scan line "i" and modulator pin "k" following the derivation of the mapping "$b_{ijk}$" discussed earlier. The actual position of the peak of each sector "$p_{ik}$" for pin "k" is used to interpolate the vector of transmission values for scan line "i" of the second scan determined using expression (1) set forth above, to calculate the transmission value "t" associated with pin "k". Each modulator pin 32 (pin "k") is then set to a new position corresponding to the appropriate modulation value "$m_{ik}$", as determined in accordance with the modulation function as in expression (2) set forth above.

Figure 10:
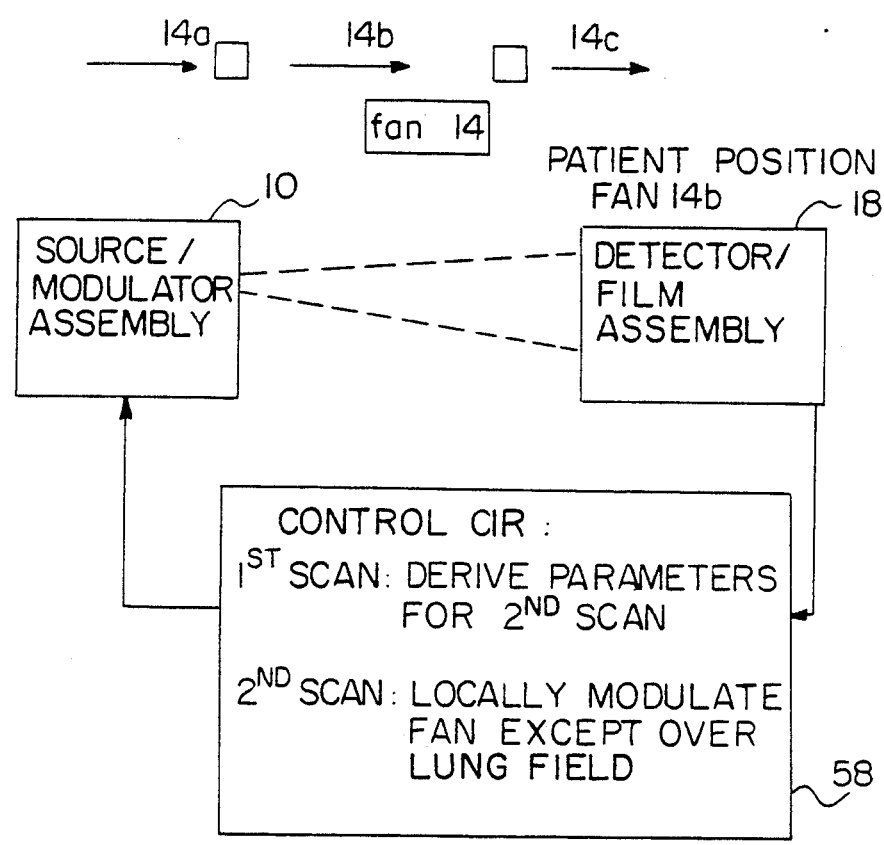
FIG. 10 is a block diagram of main components of a radiography system employing the invention.

FIG. 10 illustrates certain main components of a exemplary system embodying the invention. Components 10, 16 and 18 are as described above. Component 58 is a control circuit Which operates as described above to cause the system to carry out a first scan and derive parameters for controlling the second scan in the manner described above, and to cause the system to carry the second scan modulating everywhere except over the lung field in the manner described above. The derivation of relevant parameters discussed above is carried out by computer circuits programmed to carry out the calculations described in detail above. The input signals for the calculations are derived using known types of transducers and are converted to digital form using known techniques. The results of the calculations are converted to suitable control signals using known techniques.

As one alternative to the currently preferred embodiment, some equalization can be allowed in the selected field, different from the equalization carried out elsewhere in the same image. For example, the modulation function in the lung field can be less steep than for other fields in the image. Another alternative is to use a pre-scan flash exposure and a two-dimensional detector array, which is capable of giving a 2D map of transmission without scanning, in place of the strips of detector 52, to derive the initial patient's transmission function "$t_{ij}$" from this initial flash exposure rather than from a first scan, and to use the results to control the modulator pins in a scan corresponding to the second scan as discussed in detail above. In the last alternative, the cumulative exposure of the initial flash and the scan in the lung field should add up so a sufficient exposure level to image the lung field well but the relative contribution of the initial flash and the scan in the lung field can be divided as desired.

We claim:

1. A selective equalization imaging system comprising:
   a source of penetrating radiation;
   a control circuit causing the source to irradiate a patient with penetrating radiation and detecting radiation emerging from the patient to generate control signals identifying a lung field in the patient; and
   an imaging circuit receiving said control signals and causing the source to scan the patient with penetrating radiation at exposure controlled in accordance with said control signals to vary with position over the patient but only outside the lung field identified by said control signals.

2. A system as in claim 1, in which said control circuit comprises a mapping circuit which is operative prior to said scanning to derive a two-dimensional map of a penetrating radiation response property of the patient and for deriving said control signals as a function of said map.

3. A system as in claim 2, in which the control circuit causes the source to scan the patient with a pre-scan beam of penetrating radiation at lower exposure than at the scan caused by the imaging circuit.

4. A system as in claim 3, in which said pre-scan beam is free of local modulation.

5. A system as in claim 1, in which said source comprises a collimator defining a fan-shaped beam of penetrating radiation and a modulator comprising modulator pins which are arranged along the fan-shaped beam and selectively move into the fan-shaped beam during said scanning in accordance with said control signals to attenuate the fan-shaped beam locally and thereby to control said exposure locally.

6. A system as in claim 5, in which said modulator pins have generally triangular sections in planes parallel to that of the fan-shaped beam and the areas of the sections defined by a given plane within the fan-shaped beam increase as the pins move further into the scanning fan-shaped beam.

7. A system as in claim 1, in which said control signals define a modulation function which determines the time and extent of the local modulation of the scanning beam, and wherein said modulation function is substantially constant over the lung field.

8. A selective equalization system for imaging an object having a selected field, comprising:
   a source generating a beam of penetrating radiation scanning the object;
   a modulator for locally modulating selected portions of the scanning beam; and
   a control circuit controlling the modulator to cause the exposure which the beam delivers to the object to remain substantially constant over the selected field but to cause said exposure to vary elsewhere with selected local variations in the object.

9. A system as in claim 8, including a pre-scan circuit which causes the source to carry out a pre-scan of the object with a beam of penetrating radiation and in response to the pre-scan generates a two-dimensional map of a property of the object related to transmission of the penetrating radiation and identifying said selected field, and wherein the control circuit is responsive to said map to control the modulator.

10. A selective equalization method of imaging an object having a selected field, comprising:
    generating a beam of penetrating radiation scanning the object; and
    locally modulating portions of the scanning beam to cause the exposure which the beam of penetrating radiation delivers to the object to remain substantially constant over the selected field but to vary elsewhere with local variations in the object.

11. A method comprising the steps of:
    scanning an object position with a generally fan-shaped beam of penetrating radiation and moving, together with the scanning fan, attenuating elements which are arranged in at least one row extending in a direction transverse both to the scanning direction and to the propagation direction of the fan-shaped beam; and
    moving the respective attenuating elements into the fan-shaped beam as a function of the spatial distribution of attenuating material at the object position but only outside a selected field of the object position.

12. A method comprising:
    generating a beam of penetrating radiation scanning an object;
    locally modulating selected portions of the scanning beam;
    and
    controlling the modulating to cause the exposure which the beam delivers to the object to remain substantially constant over a selected field of the object but to vary elsewhere with selected local variations in the object.

13. A method as in claim 12, including the step of pre-scanning the object with a pre-scan beam of penetrating radiation and in response generating a two-dimensional map of a property of the object related to transmission of the penetrating radiation and identifying said selected field, and wherein the controlling step is responsive to said map to control the modulating.

14. A method as in claim 13, in which the pre-scanning beam is free of local modulation.

15. A selective equalization method of imaging an object having a selected field, comprising:
    generating a beam of penetrating radiation scanning the object; and
    locally modulating portions of the scanning beam to cause the exposure which the beam delivers to the object to remain substantially constant or to vary in a first selected manner with variations in a selected property of the object over the selected field but to vary in a second selected manner elsewhere with local variations in a selected property of the object.

16. A method as in claim 15, in which said selected property is related to the local transmission of said radiation through the object and including deriving a control signal related to the local transmission properties of the object and using said control signal to control the step of locally modulating portions of the scanning beam.

17. A method as in claim 16, in which said beam is thin in the vertical direction and wide in the horizontal direction and scans the object such that sectors of the beam move in respective vertical planes.

18. A method as in claim 15, in which the exposure is free of substantial variation over the selected field.

19. A selective equalization system for imaging an object having a selected field, comprising:
    a source generating a beam of penetrating radiation scanning the object;
    a modulator for selectively locally modulating selected portions of the scanning beam; and
    a control circuit controlling the modulator in a first manner over said selected field and in a second manner outside the selected field, said second manner of control causing the exposure which the scanning beam delivers to the object to vary with selected local variations of a property of the object.

20. A selective equalization system as in claim 19, in which said first manner of control causes the exposure which the beam delivers to the object to remain substantially constant over the selected field.

* * * * *